Jan. 9, 1940. C. C. MAYHEW Plant Pat. 352
RED CHRYSANTHEMUM PLANT
Filed Dec. 10, 1938
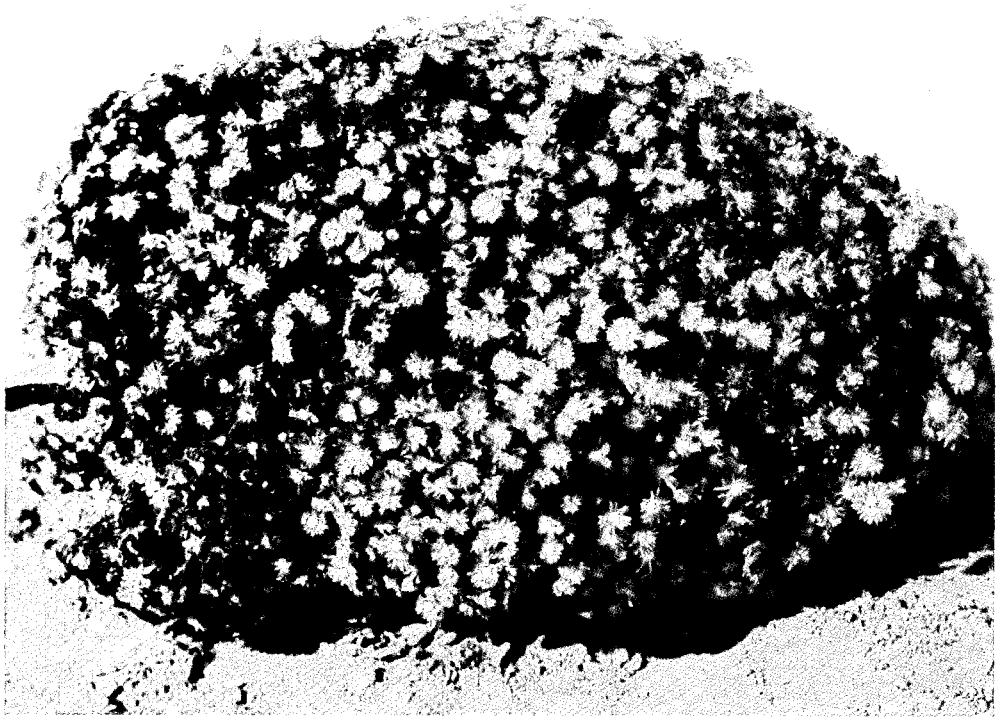
Inventor.
Clarence C. Mayhew
By Robert Robb
Attorney Patented Jan. 9, 1940

Plant Pat. 352

UNITED STATES PATENT OFFICE

352

RED CHRYSANTHEMUM PLANT

Clarence C. Mayhew, Sherman, Tex., assignor to
Texas Nursery Company, Sherman, Tex.

Application December 10, 1938, Serial No. 245,042

1 Claim. (Cl. 47—60)

My new variety of chrysanthemum is of the polyanthus type or class, the plant having a spheroidal or mound-like habit of growth and the blossoms growing many to a stem so as to completely cover the outer surface of the plant.

My new variety is dwarf in type and attains a height of from fifteen to eighteen inches ordinarily in the region of Texas. It is suitable for growing out of doors and has been found to be especially desirable for border planting and garden decoration.

The features which particularly distinguish my new variety are the color of its flowers and their shape. The color is red in general appearance and the blooms are daisy-shaped semi-double; that is, they comprise a flat disk-like center from which the petals extend spoke-like.

My new variety of chrysanthemum originated as a sport from a similar variety, a pink chrysanthemum marketed under the trade-name "Azaleamum" and was discovered as a branch growing on its parent plant which also produced the sports illustrated and described in Plant Letters Patent Nos. 204 and 205. My new variety is identical with its parent in substantially all characteristics of form, habit and growth of the plant, referring to the spheroidal or mound-like habit of growth, and the characteristic of producing many flowers to the stem and large numbers of blossoms at the outer extremities of the plant whereby substantially covering the outer surface. The color of the blooms of my new variety, however, differs from that of its parent in being red in general appearance, whereas the blossoms of the latter are pink. For further information regarding the parent, see patented files of my Plant Patents 204 and 205, also catalogs, bulletins and encyclopedias describing it under the trade names Amelia, Azaleamum, Lavender Rose, Pink Cushion.

The daisy-shaped form and semi-double arrangement of the petals of the blossoms of my new variety are also characteristics differentiating from its parent whose blossoms do not have flat centers and whose petals are arranged in a double row.

My new variety of chrysanthemum begins to bloom about 1st of October and the blooming continues until about the 10th of December, the peak of the blooming period being reached from about the middle of October to the middle of November in the region of Texas.

My new variety of chrysanthemum has been found to hold its distinguishing characteristics through succeeding generations by means of asexual reproduction, propagation being carried on from cuttings.

The following is a detailed description of my new variety of chrysanthemum:

Plant:
Mound-like in form.
Flower:
Many to a stem, of daisy-like form.
Stem:
Strong, rather short.
Quality of bloom:
Abundant—outdoors.
Continuity:
Continuous from October 1st to December 10th.
Fragrance:
Moderate, spicy.
Bloom:
When fully open is medium, one and one-half to two inches across.
Petalage:
Semi-double row on outside of flat center of bloom.
Color (compared with Ridgway's Chart):
*Buds.*—Pompeian Red (Plate XIII) blending to soft apricot yellow (Plate IV) at base.
*Flowers.*—Opening flowers shades of Jasper Red, Pompeian Red and Dragon's-blood Red (Plate XIII) with center of Lemon Chrome (Plate IV). Mature flowers Carmine Red (Plate I) at tips of petals, blending through Pompeian Red and Dragon's-blood Red (Plate XIII) to Light Orange-Yellow (Plate III) near center, which is Lemon Chrome (Plate IV).
Description of flowers made from newly opened flowers grown outdoors.
Foliage:
Moderate, dark green.
Growth:
Dwarf, spreading, much branched.

I claim:

A new and distinct variety of chrysanthemum plant, substantially as herein shown and described, characterized by the shape of its blooms and the red color of its flower.

CLARENCE C. MAYHEW.